US006451587B1

(12) United States Patent
Burns et al.

(10) Patent No.: US 6,451,587 B1
(45) Date of Patent: Sep. 17, 2002

(54) MICROBIAL ASYMMETRIC REDUCTION OF 2-CHLORO-1-[-6-(2,5-DIMETHYL-PYRROL-1-YL)-PYRIDIN-3-YL]-ETHANONE

(75) Inventors: Michael P. Burns, Mystic; John W. Wong, East Lyme, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/587,032

(22) Filed: Jun. 2, 2000

Related U.S. Application Data

(60) Provisional application No. 60/156,655, filed on Sep. 29, 1999.

(51) Int. Cl.[7] .................................................. C12P 17/12
(52) U.S. Cl. ........................ 435/280; 435/122; 435/117; 435/118
(58) Field of Search ................................ 435/280, 117, 435/118, 122

(56) References Cited

U.S. PATENT DOCUMENTS

| | | | |
|---|---|---|---|
| 5,049,497 A | 9/1991 | Kluge et al. | 435/145 |
| 5,523,223 A | 6/1996 | Kula et al. | 435/189 |
| 5,580,764 A | 12/1996 | Holt et al. | 435/118 |
| 5,618,707 A | 4/1997 | Homann et al. | 435/146 |

FOREIGN PATENT DOCUMENTS

| WO | WO9635671 | 11/1996 |
|---|---|---|

OTHER PUBLICATIONS

Patel, R.N. et al., *Enzyme Microb. Technol.*, 14: 778–784 (1992).
Patel, R.N. et al., *JAOCS*, 75 (11): 1473–1482 (1998).
Roberge, C. et al., *J. Ferment. Bioeng.*, 81(6): 530–533 (1996).
Trost, P. et al., *Eur. J. Biochem.*, 234: 452–458 (1995).
Vicenzi, J.T. et al., *Enzyme and Microbial Technology*, 20: 494–499 (1997).
Wada, M. et al., *Biosci. Biotechnol. Biochem.*, 62(2): 280–285 (1998).
Zmijewski, M.J. et al., *Appl. Microbiol. Biotechnol.*, 47(2): 162–166 (1997).
Bauer, A. et al., *Biotechnology Letters*, 18(3): 343–348 (Mar. 1996).
Bortolini, O. et al., *Tetrahedron: Asymmetry*, 9: 647–651 (1998).
Lorraine, K. et al., *Enzyme Microb. Technol.*, 19:250–255 (1996).
Madyastha, K.M. et al., *Biochemical and Biophysical Research Communications*, 211(2): 540–546 (1995).
Nakamura, K. et al., *Tetrahedron Letters*, 37(10): 1629–1632 (1996).
Nishida, T. et al., *Biocatalysis Biotransformation*, 12: 205–214 (1995).
Patel, R.N. et al., *Applied and Environmental Microbiology*, 38(2): 219–233 (1979).
Patel, R.N. et al., *Enzyme Microb. Technol.*, 13: 906–912 (1991).

*Primary Examiner*—Irene Marx
(74) *Attorney, Agent, or Firm*—Peter C. Richardson; Gregg C. Benson; Jennifer A. Kispert

(57) ABSTRACT

The present invention relates to microbial processes for carrying out the asymmetric reduction of a ketone to an alcohol, which comprises: contacting the ketone with a microorganism, or an enzyme reduction system capable of accomplishing the subject reduction comprising an enzyme derived from said microorganism and a co-factor for said enzyme, and incubating the resulting mixture under conditions sufficient to yield more of the desired (R)-enantiomer of the corresponding alcohol than the undesired (S)-enantiomer. The chiral (R)-enantiomer can be used in the synthesis of certain β-adrenergic receptor agonists.

4 Claims, No Drawings

US 6,451,587 B1

MICROBIAL ASYMMETRIC REDUCTION OF 2-CHLORO-1-[-6-(2,5-DIMETHYL-PYRROL-1-YL)-PYRIDIN-3-YL]-ETHANONE

CROSSREFERENCE TO RELATED APPLICATION

This application claims priority from U.S. Provisional Patent Application No. 60/156,655 filed Sep. 29, 1999, the benefit of which is hereby claimed under 37 C.F.R. §1.78 (a)(3).

FIELD OF THE INVENTION

The present invention relates to novel microbial processes. More specifically, the present invention provides microbial asymmetric reduction processes for preparing the alcohol (F)-2-chloro-1-[6-(2,5-dimethyl-pyrrol-1-yl)-pyridin-3-yl]-ethanol from the ketone 2-chloro-1-[6-(2,5-dimethyl-pyrrol-1-yl)-pyridin-3-yl]-ethanone. The alcohol is a known intermediate for the synthesis of certain β-adrenergic receptor agonists.

BACKGROUND OF THE INVENTION

Microbial asymmetric reductions are known which enable the selection of chirality in synthetic pathways, such as, for example, those processes disclosed in U.S. Pat. Nos. 5,049,497; 5,580,764; and 5,618,707, and in U.S. Provisional Patent Application No. 60/106,233.

U.S. Pat. No. 5,049,497 discloses a process for resolving a racemic derivative of bicyclo[4.2.0]octane by contacting the derivative with Baker's Yeast under conditions sufficient to give a mixture of a ketone and an alcohol of high enantiomeric purity. As described therein, only one enantiomer of the subject racemic ketone is reduced to give an alcohol.

U.S. Pat. No. 5,580,764 discloses an asymmetric reduction process which uses an intact microorganism, or a broken cell preparation thereof, to convert a cyclic ketone to the corresponding chiral alcohol.

U.S. Pat. No. 5,618,707 discloses a process for the stereoselective reduction of ketone substrates by adding the substrates to a culture broth of either *Zygosaccharomyces bailii* ATCC No. 38924 or *Schizosaccharomyces octosporus* ATCC No. 2479, incubating the resultant mixture, and isolating the hydroxy compound through conventional means such as, for example, extraction with organic solvents, adsorption to resins, or chromatography for subsequent use as an intermediate in the preparation of a serum cholesterol lowering agent. The isolated hydroxy compound described therein was analyzed by chiral HPLC or RP-HPLC, or both. Consistent with what would be understood by one of skill in the relevant art, as described therein, many of the large number of microorganisms which were investigated for their ability to reduce the ketone group of the selected substrate failed to reduce the ketone group with the desired specificity or productivity.

U.S. Provisional Patent Application No. 60/106,233 discloses novel microbial stereoselective reductions for preparing a key intermediate in a synthetic pathway for sertraline.

Asymmetric or enantioselective microbial reductions have also been reported in the scientific literature, such as disclosed, for example, by R. N. Patel et al., in "Microbial Synthesis of Chiral Intermediates for β-3-Receptor Agonists," *JAOCS* 75 (11): 1473–1482 (1998); by M. J. Zmijewski et al., in "Enantioselective reduction of 3,4-methylene-dioxyphenylacetone using *Candida famata* and *Zygosaccharomyces rouxii*," *Appl. Microbiol. Biotechnol.* 47(2): 162–166 (1997); by C. Roberge et al., in "Asymmetric Reduction of a Keto Ester to Its Corresponding (S)-Hydroxy Ester by Microbacterium sp. MB 5614," *J. Ferment. Bioeng.* 81(6): 530–533 (1996); by K. Lorraine et al., in "Asymmetric reduction of a ketosulfone to the corresponding trans-hydroxysulfone by the yeast *Rhodotorula rubra* MY 2169," *Enzyme Microb. Technol.* 19:250–255 (1996); and by T. Nishida et al., in "Microbial Asymmetric Reduction. Preparation of Optically Active Methyl trans-3-(4-Methoxyphenyl)glycidates," *Biocatalysis Biotransformation* 12: 205–214 (1995).

International PCT Application No. PCT/IB95/00344 published as WO 96/35671, and corresponding to U.S. patent application Ser. No. 08/945,551, discloses certain β-adrenergic receptor agonists and processes for their preparation. These agonists have utility for, inter alia, the treatment of hyperglycemia, obesity, intestinal motility disorders, depression, prostate disease, dyslipidemia, and airway inflammatory disorders such as asthma and obstructive lung disease. The agonists are also useful for increasing lean meat deposition and/or improving the lean meat to fat ratio in edible animals such as ungulate animals and poultry.

More specifically, WO 96/35671 discloses a synthetic process for the preparation of 4-(2-(2-(6-aminopyridin-3-yl)-2(R)-hydroxyethyl-amino)ethoxy)-phenylacetic acid. The majority of the β-adrenergic receptor agonist activity of this compound resides in its (R)-enantiomer. Accordingly, since the process generates a chiral diol comprising both (S)- and (R)-enantiomers, the enantiomers are preferably separated (e.g., by fractional crystallization or chromatography).

It has now been unexpectedly found that a range of microorganisms, including bacteria and fungi such as yeasts, stereoselectively reduce a ketone to its corresponding alcohol of the desired stereochemistry.

More specifically, the microbial stereoselective reductions of 2-chloro-1-[6-(2,5-dimethyl-pyrrol-1-yl)-pyridin-3-yl]-ethanone provided by the present invention result in the formation of (R)-2-chloro-1-[6-(2,5-dimethyl-pyrrol-1-yl)-pyridin-3-yl]-ethanol which can be used, for example, in the synthesis of certain of the β-adrenergic receptor agonists disclosed in WO 96/35671. The use of an intermediate having the desired stereochemistry enables an earlier committment to the desired stereochemistry of the final product and fewer steps to achieve that ultimate product.

All of the documents cited herein, including the foregoing, and any and all of the incorporated documents of the foregoing, are incorporated by reference herein in their entireties.

SUMMARY OF THE INVENTION

The present invention relates to microbiological reduction of carbonyl groups which comprises contacting an amount of a ketone compound, the compound of Formula A below, with a microorganism, or an enzyme reduction system capable of accomplishing the subject reduction comprising an enzyme derived from said microorganism and a co-factor for said enzyme, and incubating the resultant mixture under suitable conditions such that more of the compound of Formula B below than the compound of Formula C below can be formed and accumulated in the medium. The compound of Formula B is the desired corresponding alcohol of the compound of Formula A due to its having a hydroxy group of the desired stereochemistry.

The compound of Formula A ("substrate") has the following structure:

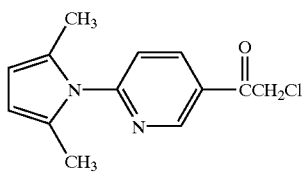

A

The desired corresponding alcohol product, the compound of Formula B, has the following structure:

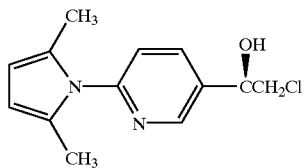

B

Where produced, the other alcohol product of the reduction, the compound of Formula C, has the following structure:

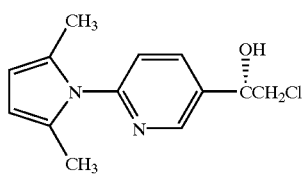

C

Accordingly, the present invention provides processes for carrying out a microbial asymmetric reduction

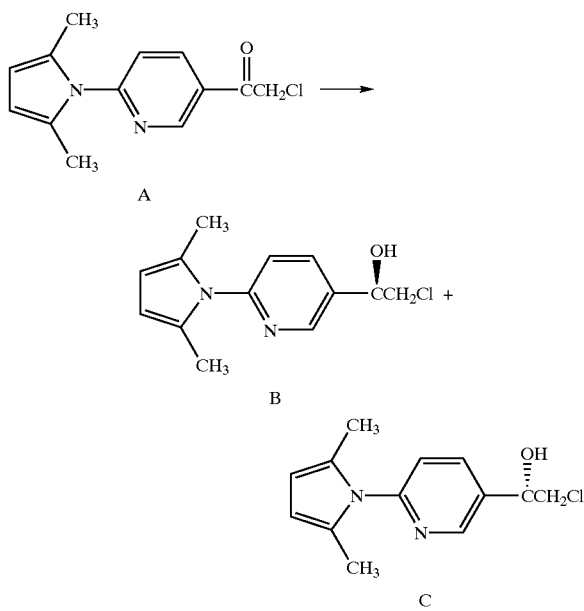

which comprises: contacting an amount of the compound of Formula A with a microorganism, or an enzyme reduction system capable of accomplishing the subject reduction comprising an enzyme derived from said microorganism and a co-factor for said enzyme, and incubating the resulting mixture under conditions sufficient to yield more of the compound of Formula B than of the compound of Formula C.

In a preferred embodiment, the microorganism is a bacterium. In a preferred embodiment wherein the microorganism is a bacterium, the bacterium is selected from the group consisting of *Rhodococcus globerulus* ATCC No. 21505, Rhodococcus sp. ATCC No. 15592, and any suitable mutants thereof.

In another preferred embodiment, the microorganism is a fungus. In a preferred embodiment wherein the microorganism is a fungus, the fungus is selected from *Mucor ambiguus* IFO 06742, *Geotrichum candidum* ATCC No. 07341, and any suitable mutants thereof.

In another preferred embodiment, the microorganism is a yeast. In a preferred embodiment wherein the microorganism is a yeast, the yeast is selected from the group consisting of *Pachysolen tannophilus* ATCC No. 32691, *Rhodotorula mucilaginosa* v. *mucilaginosa* ATCC No. 90687, *Rhodotorula mucilaginosa* v. *mucilaginosa* ATCC No. 04558, *Zygosaccharomyces bailii* ATCC No. 38924 (also deposited as PTA-660), *Rhodotorula mucilaginosa* v. *mucilaginosa* ATCC No. 36307, and any suitable mutants thereof.

In a particularly preferred embodiment wherein the microorganism is a yeast, the yeast is selected from the group consisting of *Rhodotorula mucilaginosa* v. *mucilaginosa* ATCC No. 90687, *Rhodotorula mucilaginosa* v. *mucilaginosa* ATCC No. 04558, *Zygosaccharomyces bailii* ATCC No. 38924 (also deposited with the ATCC as PTA-660), *Rhodotorula mucilaginosa* v. *mucilaginosa* ATCC No. 36307, *Rhodotorula mucilaginosa* ATCC No. 04056, and any suitable mutants thereof. In an especially preferred embodiment wherein the microorganism is a yeast, the yeast is *Zygosaccharomyces bailii* ATCC No. 38924 (also deposited with the ATCC as PTA-660).

In a preferred embodiment, the compound of Formula B is produced in an enantiomeric excess of at least about 60%. Suitable microorganisms for use in such an embodiment include: *Rhodococcus globerulus* ATCC No. 21505, Rhodococcus sp. ATCC No. 15592, *Mucor ambiguus* IFO 06742, *Geotrichum candidum* ATCC No. 07341, *Rhodotorula mucilaginosa* v. *mucilaginosa* ATCC No. 90687, *Rhodotorula mucilaginosa* v. *mucilaginosa* ATCC No. 04558, *Zygosaccharomyces bailii* ATCC No. 38924, *Zygosaccharomyces bailii* PTA-660, *Rhodotorula mucilaginosa* v. *mucilaginosa* ATCC No. 36307, and any suitable mutants thereof.

In a particularly preferred embodiment, the compound of Formula B is produced in an enantiomeric excess of at least about 80%. Suitable microorganisms for use in such an embodiment include: *Rhodococcus globerulus* ATCC No. 21505, Rhodococcus sp. ATCC No. 15592, *Rhodotorula mucilaginosa* v. *mucilaginosa* ATCC No. 90687, *Zygosaccharomyces bailii* ATCC No. 38924, *Zygosaccharomyces bailii* PTA-660, *Rhodotorula mucilaginosa* ATCC No. 04056, and any suitable mutants thereof.

In an especially preferred embodiment, the compound of Formula B is produced in an enantiomeric excess of at least about 90%. Suitable microorganisms for use in such an embodiment include: *Zygosaccharomyces bailii* ATCC No. 38924, *Zygosaccharomyces bailii* PTA-660, and any suitable mutants thereof.

In a preferred embodiment, the amount of the substrate is from about 0.1 g/L to about 20 g/L. In a particularly preferred embodiment, the amount of the substrate is from about 0.1 g/L to about 10 g/L. In an especially preferred embodiment, the amount of the substrate is about 2 g/L. In a preferred embodiment, the substrate is a compound free in solution at the time of contacting with the microorganism.

In a preferred embodiment, the substrate is added to a growth medium containing the microorganism. A preferred growth medium comprises glucose, yeast extract, soy flour, NaCl, and $K_2HPO_4$, and has a pH adjusted to about pH 7.0. A particularly preferred growth medium comprises glucose (about 20 g/L), yeast extract (5 g/L), soy flour (5 g/L), NaCl (5 g/L), and $K_2HPO_4$ (5 g/L), and has a pH adjusted to about pH 7.0 with an aqueous base, preferably NaOH.

In another preferred embodiment, said microorganism is grown in a medium comprising glucose (20 g/L), yeast extract (5 g/L), soy flour (5 g/L), NaCl (5 g/L), and $K_2HPO_4$ (5 g/L), and having a pH adjusted to about pH 7.0 with an aqueous base, preferably NaOH, for about 48 h at 29° C. and agitation, preferably 210 rpm, the substrate is then added to said growth medium, and the contacting is allowed to occur for about 24 h.

In another preferred embodiment, the substrate is added to a fermentor culture containing the microorganism. A preferred fermentor culture medium comprises glucose, yeast extract, soy flour, NaCl, $K_2HPO_4$, and aqueous TWEEN 80, and has a pH adjusted to about pH 7.0 with aqueous NaOH. A particularly preferred fermentor culture medium comprises glucose (about 20 g/L), yeast extract (5 g/L), soy flour (5 g/L), NaCl (5 g/L), $K_2HPO_4$ (5 g/L), and aqueous TWEEN 80 (0.05%), and has a pH adjusted to about pH 7.0 with an aqueous base, preferably NaOH.

In another preferred embodiment, said microorganism is added to a fermentor culture medium comprising glucose (20 g/L), yeast extract (5 g/L), soy flour (5 g/L), NaCl (5 g/L), $K_2HPO_4$ (5 g/L), and aqueous TWEEN 80 (0.05%), and having a pH adjusted to about pH 7.0 with an aqueous base, preferably NaOH, for about 48 h at 29° C. and 300 rpm and aerated at 3 Lpm, the substrate (2 g/L) is then added to said fermentor culture medium, and the contacting is allowed to occur for about 20 h.

In another preferred embodiment, the substrate is added to washed cells of the microorganism. In a preferred embodiment where the substrate is added to washed cells of the microorganism, said washed cells are resuspended in an aqueous buffered medium prior to said adding of said substrate. A preferred aqueous buffered medium is from about 50 mM to about 100 mM phosphate buffer, preferably DPBS, and has a pH adjusted to from about pH 4 to about pH 8, preferably adjusted to from about pH 4.3 to about pH 7.5, and most preferably adjusted to about pH 5.5. A particularly preferred aqueous buffered medium is about 100 mM phosphate buffer.

In a particularly preferred embodiment, a microorganism is grown in a culture medium comprising glucose, (120 g/L), yeast extract (12 g/L), malt extract (12 g/L), and peptone (20 g/L), having a pH adjusted to about pH 7 with aqueous NaOH, isolated from said growth medium, washed with 100 mM phosphate buffer having a pH adjusted to from about pH 4.3 to about pH 7.5, resuspended in said phosphate buffer, and said resuspended cells are added to a mixture of substrate, DMF, 1% aqueous TWEEN 80, and 25% aqueous glucose.

In an especially preferred embodiment, the microorganism is grown in a culture medium comprising glucose, (120 g/L), yeast extract (12 g/L), malt extract (12 g/L), and peptone (20 g/L), having a pH adjusted to about pH 7 with aqueous NaOH, for 72 h at 29° C. and 210 rpm, isolated from said growth medium, washed with 100 mM phosphate buffer having a pH adjusted to about pH 5.6, resuspended in said phosphate buffer, and said resuspended cells are added to a mixture comprising said substrate, DMF, 1% aqueous TWEEN 80, and 25% aqueous glucose, for about 21 h at 37° C. and 210 rpm.

In another especially preferred embodiment, the microorganism is grown in a culture medium comprising glucose, (120 g/L), yeast extract (12 g/L), malt extract (12 g/L), and peptone (20 g/L), for about 72 h at 29° C. and 210 rpm, isolated from said growth medium, washed with 100 mM phosphate buffer, resuspended in said phosphate buffer, and said resuspended cells are added to a mixture of said substrate, DMF, 1% aqueous TWEEN 80, and 25% aqueous glucose, for about 21 h at 37° C. and 210 rpm, said mixture is extracted with MeOH, analyzed by RP-HPLC, and the compounds of Formulae B and C are substantially isolated by flash chromatography, and analyzed by chiral HPLC.

In a preferred embodiment, the contacting of the substrate with the microorganism occurs in an aqueous medium having a pH adjusted to from about pH 3 to pH 8, preferably adjusted to from about pH 4 to pH 7, at a temperature of from about 20° C. to about 40° C., preferably at about 37° C., and with an amount of the substrate of from about 0.1 g/L to about 20 g/L, preferably with about 2 g/L.

Accordingly, the present invention also provides processes for the microbial asymmetric reduction of a compound of Formula A to the compounds of Formulae B and C which comprise: growing a microorganism in a growth medium for about 72 h at about 29° C. and about 210 rpm, said growth medium comprising glucose, yeast extract, malt extract and peptone, said growth medium having a pH of about pH 7.0, said microorganism being selected from the group consisting of *Zygosaccharomyces bailii* ATCC No. 38924, *Zygosaccharomyces bailii* PTA-660, and any suitable mutant thereof; separating said microorganism from said growth medium; washing said separated microorganism with 100 mM phosphate buffer of about pH 5.6; resuspending said washed microorganism in 100 mM phosphate buffer of about pH 5.6; contacting said resuspended microorganism with a mixture comprising an amount of said compound of Formula A, an organic solvent, a solubilizing agent, and an aqueous glucose solution; incubating said resuspended microorganism and said mixture for about 21 h at 37° C. and 210 rpm; isolating said compounds of Formulae B and C by flash chromatography; and separating said isolated compounds of Formulae B and C by crystallization.

In another preferred embodiment, the microorganism is immobilized prior to its contacting with the substrate. In a preferred embodiment where said microorganism is immobilized prior to said contacting, the cells of said immobilized microorganism are washed with an aqueous buffered medium prior to said immobilization, the immobilized washed cells are placed in an aqueous buffered medium, and the substrate is added to said aqueous buffered medium. A preferred aqueous buffered medium is the aforementioned phosphate buffer, preferably DPBS.

In another preferred embodiment the contacting of the compound of Formula A is with an enzyme reduction system. In another preferred embodiment the contacting of the compound of Formula A is with an enzyme reduction system wherein the enzyme is immobilized. In a particularly preferred embodiment the contacting of the compound of Formula A is with an enzyme reduction system derived from *Zygosaccharomyces bailii* ATCC No. 38924, *Zygosaccharomyces bailii* PTA-660, or any suitable mutant thereof.

In yet another preferred embodiment the microorganism is a broken cell preparation thereof. In yet a further preferred embodiment the microorganism is an acetone powder enzymatic preparation thereof.

In a preferred embodiment, the compound of Formula B is isolated from the medium. In a particularly preferred embodiment, the isolated compound of Formula B is used in any known synthesis of certain of the β-adrenergic receptor agonists disclosed in WO 96/35671, preferably the compound of Formula D below, 4-(2-(2-(6-aminopyridin-3-yl)-2(R)-hydroxyethyl-amino)-ethoxy)-phenylacetic acid.

D

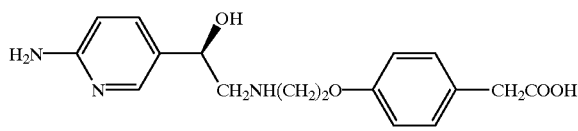

DETAILED DESCRIPTION OF THE INVENTION

Unless otherwise noted, throughout this description and the appendant claims: ° C. is degrees Celsius; % is percent; % ee is percent enantiomeric excess; ACN is acetonitrile; DMF is dimethylformamide; DPBS is Dulbecco's phosphate buffered saline; EtOAC is ethyl acetate; g is gram; h is hour or hours; HPLC is high performance liquid chromatography; L is liter; Lpm is liters per minute; MeOH is methanol; mg is milligram; min is minute or minutes; mL is milliliter; mm is millimeter; mM is millimolar (concentration); N is normal (concentration); NaOH is sodium hydroxide; RP-HPLC is reverse-phase HPLC; rpm is revolutions per minute; TFA is trifluoroacetic acid; μL is microliter; and v/v is volume per volume.

American Type Culture Collection (ATCC)—10801 University Boulevard, Manassas, Va., 20110-2209, U.S.A.

Biotage, Inc.—1500 Avon St. Ext., Charlottesville Va. 22902, U.S.A.

Chiral Technologies®, Inc.—730 Springdale Drive, P.O. Box 564, Exton, Pa. 19341, U.S.A.

Rohm and Haas®—100 Independence Mall West, Philadelphia, Pa. 19106-2399, USA.

Waters®—34 Maple Street, Milford, Mass. 01757, U.S.A.

The microorganisms disclosed herein which are available from ATCC are provided below (see, www.ATCC.com).

| | Depositor |
|---|---|
| Bacterial Culture, ATCC No. | |
| Rhodococcus sp., 15592 | Kyowa Ferm. Ind. Co., Ltd. |
| Rhodococcus globerulus, 21505 | Bioteknika Int'l., Inc. |
| Fungal Culture, ATCC No. | |
| Geotrichum candidum, 7341 | A. Castellani |
| Zygosaccharomyces bailii, 38924 | S. Goto[1] |
| Rhodotorula mucilaginosa v. mucilaginosa, 90687 | IFO-Institute for Fermentation, Osaka[2] |
| Rhodotorula mucilaginosa, 4056 | P. Redaelli |
| Rhodotorula mucilaginosa v. mucilaginosa, 36307 | NRRL[3] |
| Rhodotorula mucilaginosa v. mucilaginosa, 4558 | A. Castellani |

[1]Zygosaccharomyces bailii ATCC No. 38924 was deposited under the terms of the Budapest Treaty on September 15, 1999 and assigned deposit number PTA-660.
[2]For more information, see wwwwsoc.nacsis.ac.jp/ifo/index.html.
[3]NRRL is Northern Regional Research Laboratories (Peoria, Illinois).

Those skilled in the art will fully understand the terms used herein to describe the present invention; nonetheless, the following terms used herein, are as described immediately below.

"Co-factor" means any suitable co-factor comprising the enzyme reduction system such as, for example, NADH, NADPH, FADH, FMNH, and/or PQQ or any suitable co-factor which occurs with the enzyme in the microorganism.

"Enzyme reduction system" means a suitable microbial oxidoreductase enzyme and the reduced form of a co-factor for the oxidoreductase enzyme, where the co-factor may either be derived from the selected microorganism or may be from any suitable source. The enzyme comprising the enzyme reduction system may be in either free or immobilized form, e.g., in a column or attached to a bead.

"Microbial reduction" means the stereoselective reduction of the present invention as accomplished by the enzyme reduction system, the microbial reductase comprising the enzyme reduction system, the intact microorganism, or any preparation thereof, and the like.

"Microorganism" includes any intact microorganism or preparation therefrom, including, for example, a broken cell preparation of the microorganism; a dehydrated preparation of the microorganism, e.g., an acetone powder enzymatic preparation; microorganism washed free of, e.g., fermentation medium, culture broth, and the like; microorganism immobilized, e.g., in a column, attached to beads, and the like.

"Suitable mutants" include those microorganisms which are known or otherwise obtainable by those skilled in the relevant art and able, despite such mutation, to accomplish the stereoselective microbial reductions disclosed herein.

The present invention provides processes which comprise the microbial asymmetric reduction of the compound of Formula A to the compounds of Formulae B and C which comprises: contacting an amount of the compound of Formula A with a microorganism, or an enzyme reduction system capable of accomplishing the subject reduction comprising an enzyme derived from said microorganism and a co-factor for said enzyme, and incubating the resulting mixture under conditions sufficient to yield an amount of the compound of Formula B, whereby the amount of the compound of Formula B is greater than the amount of the compound of Formula C. Those skilled in the art will understand based upon the description provided herein how to select the conditions of the asymmetric microbial reductions of this invention such that the desired stereoselectivity is enhanced.

The desired compound of Formula B is then preferably isolated from any residual substrate and other reaction components using methods well known in the art (e.g., carried out by chromatography, preferably HPLC), prior to its preferred use as an intermediate in the aforementioned WO 96/35671 to form certain of the β-adrenergic receptor agonists described therein. For example, as exemplified in EXAMPLE III herein, the reaction mixtures can be extracted with a suitable solvent such as MeOH and analyzed by RP-HPLC; the corresponding alcohol can be separated from the other organics by flash chromatography, and the purified alcohol can be analyzed by chiral HPLC.

Generally, only a very small quantity (e.g., from about 1% ee to about 5% ee), if any, of the compound of Formula C is produced by the stereoselective microbial processes of this invention. Yet, where so desired, the amount of the compound of Formula B can be substantially separated from the amount of the compound of Formula C. For example, as exemplified in EXAMPLE II herein, the enantiomers of the purified alcohol are substantially separated and the separation is carried out by crystallization.

The processes of the present invention are readily carried out. Thus, the microorganism is either fermented (intact microorganism) or incubated (broken cell preparation, dehydrated preparation, or any other suitable preparation of the microorganism) in the presence of an amount of the substrate, represented by Formula A, to produce a greater amount of the desired product, the (R)-enantiomer of the corresponding alcohol, represented by Formula B, than the undesired (S)-enantiomer of the corresponding alcohol, thereby, in one step, resulting in the optically enriched (R)-enantiomer of the corresponding alcohol. As discussed above, the (R)-enantiomer may then be further reacted by methods well known to those skilled in the relevant art such as described, for example, in the WO 96/35671, counterpart U.S. patent application Ser. No. 08/945,551, and U.S. Provisional Patent Application No. 60/145,417, to ultimately yield a desired β-adrenergic receptor agonist.

The activity, methods for testing activities, dosages, dosage forms, methods of administration and background information concerning the β-adrenergic receptor agonists are set forth, for example, in WO 96/35671, its counterpart U.S. patent application Ser. No. 08/945,551, and U.S. Provisional Patent Application No. 60/145,417.

One or more of any suitable microorganism may be used in the processes of the present invention. As described earlier, the microorganism used in the subject processes may be intact, any suitable preparation thereof, e.g., a broken cell preparation thereof, a dehydrated preparation thereof, and be either free or immobilized. However, where a non-intact microorganism is employed in the present invention such as, for example, a broken cell preparation, e.g., cell extract, acetone powder enzymatic preparation, or the enzyme derived therefrom, those skilled in the art would understand that a suitable co-factor for the enzyme is also included.

Those skilled in the art will understand from the description provided herein and their related knowledge how to prepare a suitable broken cell preparation such as described, for example, by R. N. Patel et al. in the article "Oxidation of Secondary Alcohols to Methyl Ketones by Yeasts" published in *Applied and Environmental Microbiology*, 38(2): 219–223 (1979).

Those skilled in the art will understand from the description provided herein and their related knowledge how to prepare a suitable acetone powder enzymatic preparation such as described, for example, by K. Nakamura et al. in the article "Asymmetric Reduction of Ketones by the Acetone Powder of *Geotrichum candidum*" published in *Tetrahedron Letters*, 37(10): 1629–1632 (1996).

In addition, an enzyme (e.g., an oxidoreductase) of any suitable microorganism may also be used in the subject processes, and this enzyme may be isolated from the microorganism by any suitable method known to those skilled in the art and, as for the intact microorganism, may be used in the subject process in either free or immobilized form. Those skilled in the art will understand from the description provided herein and their related knowledge how to isolate and purify the enzyme of the suitable microorganism such as generally described, for example, in the articles by: M. Wada et al., "Purification and Characterization of NADPH-Dependent Carbonyl Reductase, Involved in Stereoselective Reduction of Ethyl 4-Chloro-3-oxobutanoate, from *Candida magnoliae*" published in *Biosci. Biotechnol. Biochem*, 62(2): 280–285 (1998), P. Trost et al., "Purification and Properties of NAP(P)H:(quinone-acceptor) oxidoreductase of sugarbeet cells" published in *Eur. J. Biochem.*, 234: 452–458 (1995), K. M. Madyastha and T. L. Gururaja, "Purification and Some of the Properties of a Novel Secondary Alcohol Dehydrogenase from Alcaligenes eutrophus" published in *Biochemical and Biophysical Research Communications*, 211(2): 540–546 (1995), O. Bortolini et al., "Kinetic resolution of vic-diols by *Bacillus stearothermophilus* diacetyl reductase" published in *Tetrahedron: Asymmetry*, 9: 647–651 (1998), R. N. Patel et al., "Stereospecific microbial reduction of 4,5-dihydro-4-(4-methoxyphenyl)-6-(triflurormethyl-1H-1)-benzazepin-2-one" published in *Enzyme Microb. Technol.*, 3: 906–912 (1991) and R. N. Patel et al., "Stereoselective microbial/enzymatic oxidation of (exo, exo)-7-oxabicyclo[2.2.1] heptane-2,3-dimethanol to the corresponding chiral lactol and lactone" published in *Enzyme Microb. Technol.*, 14: 778–784 (1992); and by U.S. Pat. No. 5,523,223 and the aforementioned U.S. Pat. No. 5,580,764.

Suitable microorganisms include *Rhodococcus globerulus* ATCC No. 21505, Rhodococcus sp. ATCC No. 15592, *Mucor ambiguus* IFO 06742, *Geotrichum candidum* ATCC No. 07341, *Pachysolen tannophilus* ATCC No. 32691, *Rhodotorula mucilaginosa* v. *mucilaginosa* ATCC No. 90687, *Rhodotorula mucilaginosa* v. *mucilaginosa* ATCC No. 04558, *Zygosaccharomyces bailii* ATCC No. 38924 (also deposited with the ATCC as PTA-660), *Rhodotorula mucilaginosa* v. *mucilaginosa* ATCC No. 36307, *Rhodotorula mucilaginosa* ATCC No. 04056, and any suitable mutants thereof.

Preferred microorganisms are those which produce an enantiomeric excess of the (R)-enantiomer, the compound of Formula B, where the excess is at least about 60%. Particularly preferred are those which produce an enantiomeric excess of the (R)-enantiomer, the compound of Formula B, where the excess is at least about 80%. Especially preferred microorganisms are those which produce an enantiomeric excess of the (R)-enantiomer, the compound of Formula B, where the excess is at least about 90%. Those skilled in the art will understand from the present description how to determine for each selected microorganism the amount of enantiomeric excess of the (R)-enantiomer.

The microorganisms suitable for use in the subject stereoselective microbial reduction may be prepared by any suitable method known to those skilled in the relevant art. An example of a suitable method for the preparation of a microorganism from a commercially purchased stock is provided below. The method provided below may be used for any microorganism suitable for use in the present inventive process, and those skilled in the art would understand from the description provided herein how to modify any part of the procedure, e.g., method of preparing the microorganism, free or immobilized, washed or unwashed; method of contacting of the amount of the substrate with the microorganism; growth medium components and conditions, e.g., temperature, pH and the like; or incubation conditions, to achieve the desired result in any particular process.

Those skilled in the art will understand from the description provided herein how to prepare suitable immobilized microorganism such as described, for example, by A. Bauer et al. in the article "Polyvinyl alcohol-immobilized whole-cell preparations for biotransformation of nitriles" published in *Biotechnology Letters*, 18(3): 343–348 (March 1996).

Any suitable method of contacting the amount of the substrate with the microorganism or enzyme reduction system may be used in the present invention. The substrate may be contacted with the microorganism or the enzyme reduction system in any suitable order. For example, the substrate may be added to a medium, such as a culture broth, comprising the microorganism, free or immobilized, or some combination thereof; or the medium may comprise the substrate and the microorganism may then be added to such medium; or the substrate and the microorganism may be added together to such medium; or the substrate may be added to a broken cell preparation thereof; or the substrate may be added to a dehydrated preparation of the microorganism; or either the substrate or the microorganism or enzyme reduction system may be added to a suitable solvent comprising the other; and the like. For example, the enzyme reduction system may be added to an appreciably organic solvent with the contacting occurring by adding the substrate to that solvent. Those skilled in the art would also understand based on the present description how to contact by adding the substrate adsorbed to a resin. Moreover, those skilled in the art will understand from the description provided herein how to modify any part of the subject process as desired.

It is especially preferred in the present invention that the microorganism or enzyme reduction system is derived from *Zygosaccharomyces bailii* ATCC No. 38924. A frozen sample of *Zygosaccharomyces bailii* ATCC No. 38924 was deposited with the ATCC, under the terms of the Budapest Treaty on Sep. 15, 1999. This newly deposited culture was given the new deposit number PTA-660. Hence, it is also especially preferred in the present invention that the microorganism is *Zygosaccharomyces bailii* PTA-660 and any suitable mutants thereof. All restrictions on the availability to the public of the microorganism culture so deposited will be irrevocably removed upon the issuance of a patent from the specification of the present invention.

Cultures of *Zygosaccharomyces bailii* ATCC No. 38924 can be obtained from the ATCC, and an example of a suitable method for its preparation from such a commercially purchased stock is provided immediately below. A culture so obtained is added to a suitable growth medium, and is incubated with shaking until growth occurs, both steps as would be appreciated by those skilled in the art. The culture, thus prepared, can be used to inoculate slants, with portions of these slants frozen as master stocks. Alternatively, liquid stock cultures can be prepared to which glycerol is added to from about 10% to about 20% which are then frozen at about −80° C., preferably in small cryotubes.

As would be understood by those skilled in the art for any microorganism selected, and as provided specifically hereinafter in the examples for *Zygosaccharomyces bailii* ATCC No. 38924 or PTA-660, a suitable method for preparing the microorganism is as follows: the microorganism is inoculated from a frozen stock culture such as described above (about a 17% glycerol stock) into a flask or a glass tube with a metal closure containing a growth medium (containing an aliquot from a sterile solution which includes Tween® 80, glycerol and distilled water) whose composition is described in more detail below. The fermentation is carried out at temperatures ranging from about 22° C. to about 32° C., and preferably at about 29° C., with suitable shaking, preferably from about 200 rpm to about 220 rpm, and most preferably, at about 210 rpm. Where so desired, the pH of the growth medium can be maintained by the use of suitable buffers incorporated into the fermentation medium and/or periodically adjusted by addition of either base, preferably NaOH, or acid as so required.

Any suitable duration of growth of the microorganism, contacting of the microorganism with the amount of the substrate, and incubation of the substrate with the microorganism may be used in the present invention. Suitable growth of the microorganism may be achieved, e.g., within about 24 h, 48 h, or 72 h, at which time a suitable aliquot of a solution of the amount of the substrate in a suitable solvent, preferably ethanol, may be added to the culture. The fermentation may then be continued for, e.g., from about two to about six days, and preferably, e.g., for about five days, at which time the fermentation broth may be extracted using any suitable extraction method whereby, for example, a suitable solvent, such as, for example, EtOAc, methyl isobutylketone, methyl ethylketone, methylene chloride, and the like, preferably, EtOAc, removes the organic components from the fermentation broth. As discussed above, MeOH can also be used to extract material from the cells into the MeOH-water mixture. After extraction of the fermentation broth and separation of the organic and aqueous phases, the compounds comprising the organic residue may be determined using any suitable method, such as, for example, chromatography, preferably, chiral HPLC.

As described above, the contacting can be by adding the substrate adsorbed to a resin. See, for example, the article by J. T. Vicenzi et al., "Large-scale stereoselective enzymatic ketone reduction with in situ product removal via polymeric adsorbent resins," *Enzyme and Microbial Technology*, 20: 494–499 (1997).

Any suitable growth medium may be used in the process of the present invention, and the suitable growth medium will contain a source or sources of assimilable carbon, assimilable nitrogen and inorganic salts containing essential minerals. In general, many carbohydrates such as, for example, glucose, maltose, mannose, sucrose, starch, glycerin, millet jelly, molasses, soy bean, and the like, can be used as sources of assimilable carbon. Sources of assimilable nitrogen include, for example, materials such as yeast and casein hydrolysates, primary yeast, yeast extracts, cottonseed flour, soybean solids, wheat germ, meat extracts, peptone, corn steep liquor, and ammonium salts. Suitable inorganic salt nutrients for use in the culture medium of the present invention include, for example, the customary salts containing sodium, iron, magnesium, potassium, cobalt, phosphate, and the like.

More particularly, growth media suitable for use in the present invention include, for example, a media comprising: (a) dextrose (about 20 g), yeast extract (about 5 g), soy flour (about 5 g), NaCl (about 5 g), $K_2HPO_4$ (about 5 g), and distilled $H_2O$ (about 1 L), pH adjusted to about pH 7.0 with $H_2SO_{4(aq.)}$. Those skilled in the art will understand from, for example, the *Handbook of Microbial Media* by R. M. Atlas, edited by L. C. Parks, CRC Press, Inc., 1993, based upon this description, how to select a suitable medium for any particular microorganism of this invention. A preferred growth medium includes: glucose (about 20 g/L), yeast extract (5 g/L), soy flour (5 g/L), NaCl (5 g/L), and $K_2HPO_4$ (5 g/L), pH adjusted to about 7.0 with an aqueous base, preferably NaOH. A preferred growth medium for *Zygosaccharomyces bailii* ATCC No. 38924 and *Zygosaccharomyces bailii* PTA-660 includes: glucose (about 120 g/L), yeast extract (about 12 g/L), malt extract (about 12 g/L), and peptone (about 20 g/L). An especially preferred growth medium for *Zygosaccharomyces bailii* ATCC No. 38924 and *Zygosaccharomyces bailii* PTA-660 includes: glucose (about 120 g/L), yeast extract (about 12 g/L), malt extract (about 12 g/L), and peptone (about 20 g/L), pH adjusted to about 7.0 with an aqueous base, preferably NaOH.

Reference to particular buffers, media, reagents, contacting or culture conditions, and the like, is not intended to be limiting, but should be read to include all such related materials that those of ordinary skill in the art would recognize as being of interest or value in the particular context in which the description herein is presented. For example, it is often possible to substitute one buffer system or culture medium for another, such that a different but known way is used to achieve the same goals as those to which the use of a suggested method, material or composition is directed. Moreover, it should be understood that the present invention includes the scaling-up of the subject process for commercial purposes.

Hence, as would be understood by those of ordinary skill in the art, variation of the growth medium, the conditions of fermentation, and/or the conditions of the reduction (e.g., the temperature, pH, and the amount of substrate (i.e. the substrate) may be altered to control the yield of the resultant compounds and their relative rates of production. In general, the techniques employed in the present invention will be chosen with regard to industrial efficiency. The growth media, conditions of fermentation and relative amounts of microorganism, or enzyme reduction system, and of the substrate described herein, are merely illustrative of the wide variety of media, fermentation conditions and amounts of starting materials which may be suitably employed in the present invention as would be appreciated by those skilled in the art, and are not intended to be limiting in any way.

Any suitable methods for isolating and/or purifying any of the products of the subject processes may be used in the present invention including filtration, extraction, crystallization, column chromatography, thin-layer chromatography, preparative low pressure liquid chromatography or HPLC, or any suitable combination of such methods. As discussed above, the compounds of Formulae B and C are preferably substantially isolated (e.g., at least about 40%), and the isolation is preferably carried out by chromatography (e.g., flash chromatography). In addition, the isolated compounds of Formulae B and C are preferably substantially separated (e.g., at least about 60%), and the separation is preferably carried out by crystallization.

The compound of Formula B can be adsorbed from the reaction mixture onto a resin, preferably a polymeric adsorbent resin, eluted therefrom using a suitable organic solvent, preferably EtOAc, and crystallized from the eluted material using a suitable organic solvent, or a combination of suitable organic solvents, preferably EtOAc and MeOH. More specifically, the reaction medium (e.g., culture broth) can be extracted using any suitable extraction method, for example, (a) whereby a suitable solvent, such as, for example, EtOAc, methyl isobutylketone, methyl ethylketone, methylene chloride, and the like, preferably, EtOAc, removes the organic components from the reaction medium, or (b) by adsorption of the products, the compounds of Formula B and C, onto a suitable resin, preferably a polymeric adsorbent resin, more preferably a resin selected from those of the tradename Amberlite® (Rohm and Haas), most preferably XAD4 (of the Amberlite resins) and, after extraction of the reaction medium with a suitable organic solvent and separation of the organic and aqueous phases, the compounds comprising the organic residue may be determined using any suitable method, such as, for example, chromatography.

The detailed examples provided below show that a range of microorganisms, including bacteria and fungi, e.g., yeasts, stereoselectively reduce the ketone of Formula A, to yield the desired (R)-enantiomer of the corresponding alcohol of Formula B, and substantially less, if any, of the undesired (S)-enantiomer of the corresponding alcohol of Formula C, which may then be separated from each other and the compound of Formula B further reacted according to methods well known in the art to yield, e.g., certain of the β-adrenergic receptor agonists disclosed in WO 96/35671, its counterpart U.S. patent application Ser. No. 08/945,551, preferably 4-(2-(2-(6-aminopyridin-3-yl)-2(R)-hydroxyethyl-amino)-ethoxy)-phenylacetic acid (the compound of Formula D), and co-pending U.S. Provisional Patent Application No. 60/145,417 which also discloses novel processes for preparing the compound of Formula D.

The present invention is illustrated by the following EXAMPLES. The foregoing and following description of the present invention and the various embodiments are not intended to be limiting of the invention but rather are illustrative thereof. Hence, it will be understood that the invention is not limited to the specific details of these EXAMPLES.

EXAMPLE I

REDUCTION OF THE COMPOUND OF FORMULA A USING BACTERIA, FUNGI, AND YEAST

Each of the organisms of TABLE 1 was grown in a medium containing glucose, 20 g/L; yeast extract, 5 g/L; soy flour, 5 g/L; NaCl, 5 g/L, and $K_2HPO_4$, 5 g/L, pH adjusted to 7.0 with aqueous NaOH prior to sterilization. For each organism, a test tube (16×125 mm) containing 2.5 mL of medium was inoculated with the organism (25 μL of a 17% frozen glycerol stock) and incubated on a rotary shaker for 48 h at 29° C. and 210 rpm. Substrate, the compound of Formula A, was added to a concentration of 0.1 g/L by adding 25 μL of a 10 g/L ethanolic solution. After 24 h, the cultures were acidified with 25 μL of 4N HCl and extracted with 5 mL EtOAc. The EtOAc extract was dried under a stream of nitrogen and analyzed by RP-HPLC and chiral HPLC. The RP-HPLC method consisted of a Symmetry® $C_{18}$, 5 μm, 3.9×150 mm column (Waters) running isocratically at 1 ml/min with 55% aqueous TFA (0.05%): 45% ACN or a Symmetry $C_{18}$, 3.5 μm, 4.6×50 mm column running at 1.5 mL/min with the same solvent system. The chiral HPLC method consisted of a Chiralpak® AD, 4.6× 250 mm column (Chiral Technologies Inc.) running isocratically at 1.2 mL/min with 92% hexane: 8% isopropanol. The percent yield of the corresponding alcohol and the enantiomeric excess of the (R)-enantiomer of the alcohol, the compound of Formula B, are shown in TABLE 1.

TABLE I

| CULTURE | % CONVERSION to corresponding alcohol | R-CONFIGURATION, (% ee) |
|---|---|---|
| Rhodococcus sp., ATCC No. 15592, bacterium | 44.8 | 81.1 |
| Rhodococcus globerulus, ATCC No. 21505, bacterium | 45.2 | 79.8 |
| Geotrichum candidum, ATCC No. 7341, fungus | 22.4 | 63.2 |
| Mucor ambiguus IFO 06742, fungus | 32.0 | 61.7 |
| Zygosaccharomyces bailii, ATCC No. 38924, yeast | 38.0 | 91.3 |
| Rhodotorula mucilaginosa v. mucilaginosa, ATCC No. 90687, yeast | 49.2 | 83.1 |
| Rhodotorula mucilaginosa, ATCC No. 4056, yeast | 20.0 | 80.2 |
| Rhodotorula mucilaginosa v. mucilaginosa, ATCC No. 36307, yeast | 25.6 | 73.2 |
| Rhodotorula mucilaginosa v. mucilaginosa, ATCC No. 4558, yeast | 40.0 | 70.4 |

The results from the chiral analysis show, in part, that the *Zygosaccharomyces bailii* ATCC No. 38924 culture substantially reduces the ketone of Formula A to the desired (R)-enantiomer of the corresponding alcohol, the compound of Formula B, which was determined to be present in about 91.3% ee by such chiral HPLC.

Accordingly, the inclusion of the microorganism, i.e., *Zygosaccharomyces bailii* ATCC No. 38924, resulted in the production of a greater amount of the corresponding alcohol having a hydroxyl group of the desired stereochemistry than of the undesired stereochemistry.

EXAMPLE II

REDUCTION OF THE COMPOUND OF FORMULA A WITH A FERMENTOR CULTURE USING *Zygosaccharomyces bailii* ATCC NO. 38924

A culture of *Zygosaccharomyces bailii* ATCC No. 38924 was grown in a medium containing glucose, 20 g/L; yeast extract, 5 g/L; soy flour, 5 g/L; NaCl, 5 g/L, and $K_2HPO_4$, 5 g/L, pH adjusted to 7.0 with aqueous NaOH prior to sterilization. A 3 L Fernbach flask containing 500 mL of inoculum culture was incubated on a rotary shaker for 48 h at 29° C. and 210 rpm. This seed culture was used to inoculate 8 L of the same medium that also contained TWEEN 80 at 0.05%. The fermentor culture was incubated for 48 h at 29° C., 300 rpm, and 3 Lpm aeration. The substrate, the compound of Formula A, was then added to yield an initial concentration of 2 g/L and the reaction proceeded for an additional 20 h. After analysis by HPLC revealed an 89% yield by weight of the corresponding alcohol, 750 g of Amberlite XAD-4 resin was added. This mixture was stirred at room temperature overnight and filtered through a #80 mesh (180 micron) sieve. The resin was retained by the sieve, and the culture broth, including the cells, passed through the sieve and was discarded. The resin was washed with 8 L of water and then eluted with 8 L of EtOAc. The EtOAc eluate was washed with water, dried over $MgSO_4$, dried under reduced pressure, and analyzed by RP- and chiral HPLC. The (R)-enantiomer of the corresponding alcohol, the compound of Formula B, was present in 98.7% ee. The alcohol was purified by flash chromatography on silica gel (Biotage KP-SIL, Biotage, Inc.) with EtOAc: hexane (20:80 v/v) and crystallized from EtOAc: hexane to yield 12.7 g of the substantially optically pure (R)-alcohol.

EXAMPLE III

REDUCTION OF THE COMPOUND OF FORMULA A USING WASHED CELLS OF *Zygosaccharomyces bailii* ATCC NO. 38924

A culture of *Zygosaccharomyces bailii* ATCC No. 38924 was grown in a medium containing glucose, 120 g/L; yeast extract, 12 g/L; malt extract, 12 g/L; and peptone, 20 g/L. One 300 mL Erlenmeyer flask, containing 100 mL of culture was incubated for 72 h at 29° C. and 210 rpm on a shaking incubator. After incubation, the cells were separated by centrifugation, washed with 50 mL of 100 mM phosphate buffer (pH 5.6), and resuspended to 12.5 mL using the same phosphate buffer. A 1.25 mL portion of this was added to a mixture of 50 mg of substrate, the compound of Formula A, 0.125 mL of DMF, 1.25 mL of 1% aqueous TWEEN 80, and 0.4 mL of 25% aqueous glucose in a 16×125 mm test tube. Duplicate tubes were incubated for 21 h at 37° C. and 210 rpm on a shaking incubator. After incubation, the reaction mixtures were extracted with MeOH and analyzed by RP-HPLC as described in the aforementioned EXAMPLE II. The corresponding alcohol was separated from the DMF by flash chromatography on a $C_{18}$ SepPak® (Waters) using an ACN:water gradient. The purified alcohol was then analyzed by chiral HPLC as described in the aforementioned EXAMPLE II. A 76% yield (by weight) of the corresponding alcohol in 98.7% ee, favoring the (R)-enantiomer, the compound of Formula B, was realized.

What is claimed is:

1. A process for the microbial asymmetric reduction of a compound of Formula A to the compounds of Formulae B and C

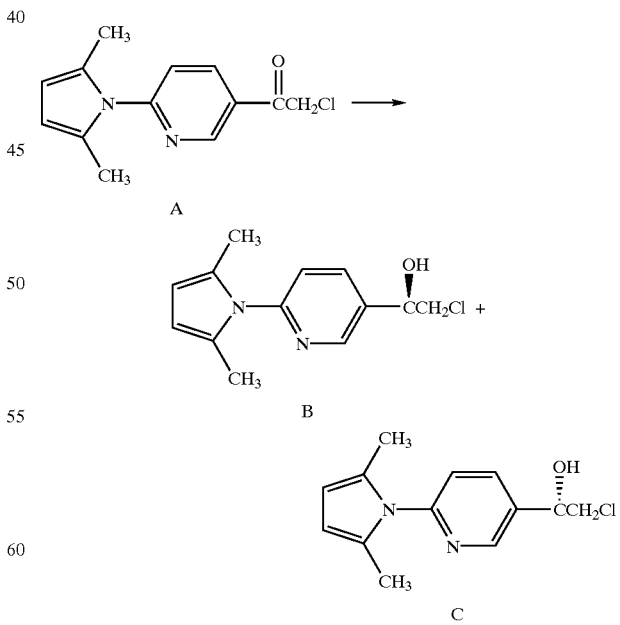

which comprises:
  contacting an amount of said compound of Formula A with a microorganism selected from the group consisting of: Rhodococcus sp. ATCC No. 15592, Rhodococcus globerulus ATCC No. 21505, Geotrichum candidum ATCC No. 7341, Mucor ambiguus IFO 06742, Zygosaccharomyces bailii ATCC No. 38924, Zygosaccharomyces bailii PTA-660, Rhodotorula mucilaginosa v. mucilaginosa ATCC No. 90687, Rhodotorula mucilaginosa ATCC No. 04056, Rhodotorula mucilaginosa v. mucilaginosa ATCC No. 36307, Rhodotorula mucilaginosa v. mucilaginosa ATCC No. 4558, and any mutants thereof capable of accomplishing said reduction;

incubating the resulting mixture under conditions sufficient to yield at least about a 60% enantiomeric excess of said compound of Formula B; and recovering said compound of Formula B.

2. The process as defined in claim 1 wherein said microorganism is selected from the group consisting of: Rhodococcus sp. ATCC No. 15592, Rhodococcus globerulus ATCC No. 21505, Zygosaccharomyces bailii ATCC No. 38924, Zygosaccharomyces bailii PTA-660, Rhodotorula mucilaginosa V. mucilaginosa ATCC No. 90687, Rhodotorula mucilaginosa ATCC No. 04056, and said mutants thereof.

3. The process as defined in claim 2 wherein said microorganism is selected from the group consisting of: Zygosaccharomyces bailii ATCC No. 38924, Zygosaccharomyces bailii PTA-660, and said mutants thereof.

4. A process for the microbial asymmetric reduction of a compound of Formula A to the compounds of Formulae B and C

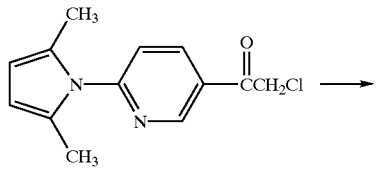

A

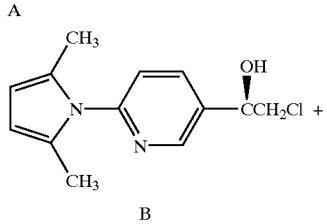

B

-continued

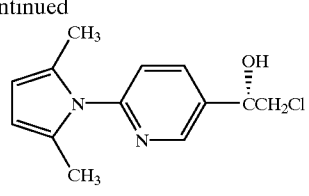

C which comprises, in sequence:

growing a microorganism in a growth medium for about 72 h at about 29° C. and about 210 rpm, said growth medium comprising glucose, yeast extract, malt extract and peptone, said growth medium having a pH of about pH 7.0, said microorganism being selected from the group consisting of: Zygosaccharomyces bailii ATCC No. 38924, Zygosaccharomyces bailii PTA-660, and any mutants thereof capable of accomplishing said reduction;

separating said microorganism from said growth medium;

washing said separated microorganism with 100 mM phosphate buffer of about pH 5.6;

resuspending said washed microorganism in 100 mM phosphate buffer of about pH 5.6;

contacting said resuspended micoorganism with a mixture comprising an amount of said compound of Formula A, an organic solvent, a solubilizing agent, and an aqueous glucose solution;

incubating said resuspended microorganism and said mixture for about 21 h at about 37° C. and about 210 rpm; and recovering said compound of Formula B by isolating said compounds of Formulae B and C by flash chromatography and separating said isolated compounds of Formulae B and C by crystallization.

* * * * *